(12) United States Patent
Lovatt (10) Patent No.: US 10,292,393 B2
(45) Date of Patent: May 21, 2019

(54) MITIGATION OF ALTERNATE BEARING

(71) Applicant: The Regents of the University of California, Oakland, CA (US)

(72) Inventor: Carol J. Lovatt, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/728,964

(22) Filed: Jun. 2, 2015

(65) Prior Publication Data

US 2016/0021885 A1 Jan. 28, 2016

Related U.S. Application Data (63) Continuation of application No. 13/519,888, filed as application No. PCT/US2010/062268 on Dec. 28, 2010, now Pat. No. 9,044,018.

(60) Provisional application No. 61/290,470, filed on Dec. 28, 2009.

(51) Int. Cl.
| | | |
|---|---|---|
| *A01N 43/90* | (2006.01) | |
| *A01N 57/16* | (2006.01) | |
| *C05B 15/00* | (2006.01) | |
| *C05F 11/10* | (2006.01) | |

(52) U.S. Cl.
CPC ............ *A01N 43/90* (2013.01); *A01N 57/16* (2013.01); *C05B 15/00* (2013.01); *C05F 11/10* (2013.01)

(58) Field of Classification Search
None
See application file for complete search history.

(56) References Cited

U.S. PATENT DOCUMENTS

| | | | |
|---|---|---|---|
| 3,830,643 A | 8/1974 | Schneider et al. | |
| 4,209,316 A | 6/1980 | McDaniel et al. | |
| 4,741,754 A | 5/1988 | Ries | |
| 5,009,698 A | 4/1991 | Ries et al. | |
| 5,217,738 A | 6/1993 | Ries | |
| 5,234,898 A | 8/1993 | Ries | |
| 6,169,057 B1 | 1/2001 | Lovatt | |
| 6,180,569 B1 | 1/2001 | Lovatt | |
| 6,874,277 B2 | 4/2005 | Yamashita | |
| 6,929,673 B1 | 8/2005 | Lovatt | |
| 7,160,350 B2 | 1/2007 | Lovatt | |
| 8,846,572 B2 | 9/2014 | Lovatt | |
| 9,044,018 B2 * | 6/2015 | Lovatt ................ | A01N 43/90 |
| 9,603,366 B2 | 3/2017 | Lovatt | |
| 2002/0106388 A1 * | 8/2002 | Pugliese ................ | A61K 8/44 |
| | | | 424/401 |
| 2002/0121046 A1 | 9/2002 | Yamashita | |
| 2004/0192553 A1 | 9/2004 | Kurauchi et al. | |
| 2004/0209777 A1 | 10/2004 | Gemma et al. | |
| 2017/0325456 A1 | 11/2017 | Lovatt | |

FOREIGN PATENT DOCUMENTS

| | | |
|---|---|---|
| EP | 0190885 A2 | 8/1986 |
| EP | 0199474 A2 | 10/1986 |
| EP | 0508777 A2 | 10/1992 |
| JP | 48-26517 Y1 | 8/1973 |
| JP | 48-67051 A | 9/1973 |
| JP | 54-17670 B | 7/1979 |
| JP | 62-249979 A | 10/1987 |
| JP | 2013-515501 A | 5/2013 |
| WO | 79/00838 A1 | 10/1979 |
| WO | 2011/090726 A2 | 7/2011 |
| WO | 2011/090727 A2 | 7/2011 |
| WO | 2011/090726 A3 | 11/2011 |
| WO | 2011/090727 A3 | 11/2011 |

OTHER PUBLICATIONS

Kessler et al.( Flowering in fruit trees and annual plants as affected by purines, pyrimidines and triiodobenzoic acid, Plant Physiol, (1959) vol. 34, No. 6, pp. 605-608). (Year: 1959).*
Sun et al.( Quantitative determination of rutin, quercetin,and adenosine, rutin, quercetin, and adenosine in Flos carthami by capillary electrophoresis, Journal of Separation Science (2003), (Year: 2003).*
Sun et al.( Determination of adenosine, rutin and quercetin in Carthamus tinctorius by HPCE, Yaoxue Xuebao (2003),38(4), 283-285). (Year: 2003).*
Kurebayashi et al.( Characterization of increased calcium efflux by quercetin from the sarcoplasmicreticulum in frog skinned skeletal muscle fibers, Journal of Muscle Research and Cell Motility (1986), 7(2), 142-50). (Year: 1986).*
Hu et al.( Secondary metabolites in a soybeanfermentation broth of Paecilomyces militaris, Food chemistry (2009),vol. 116, No. 1, pp. 198-201). (Year: 2009).*
Chen et al.( On the ability of four flavonoids,baicilein, luteolin, naringenin, and quercetin, to suppress the fenton reaction of the iron-ATP complex, BioMetals (2000), 13(1), 77-83). (Year: 2000).*
Bukovac et al., "Modifying Alternate Bearing of Spur-Type 'Delicious' Apple with Ethephon", HortScience. vol. 41, No. 7, 2006, pp. 1606-1611.
Dixon et al., "The Impact of Foliar Applications of Nitrogen and Boron on 'Hass' Avocado Fruit Set in 2004", New Zealand Avocado Grower's Association Annual Research Report, vol. 5, 2005, pp. 27-34.

(Continued)

*Primary Examiner* — Alton N Pryor
(74) *Attorney, Agent, or Firm* — Morrison and Foerster LLP (57) ABSTRACT

Described are compositions and methods to mitigate alternate bearing of perennial crops by use of a natural metabolite. In particular, the present disclosure provides a natural metabolite in the presence or absence of an auxin transport inhibitor to increase floral intensity (flower number) of the return bloom in the spring following the setting of a heavy on-crop to increase the yield of the putative off-crop year and, thus, increase cumulative crop yield. Additionally the present disclosure provides a natural metabolite in combination with one or both of a growth promoting type of plant growth regulator, and a hormone biosynthesis, transport or function inhibiting type of plant growth regulator.

12 Claims, 2 Drawing Sheets

(56) References Cited

OTHER PUBLICATIONS

Extended European Search Report (includes Supplementary European Search Report and Search Opinion) received for European Patent Application No. 10844272.4, dated Apr. 8, 2014, 8 pages.
Extended European Search Report received for European Patent Application No. 10844271.6, dated Jul. 8, 2013, 6 pages.
Gonzalez et al., "Properly Timed Foliar Fertilization Can and Should Result in a Yield Benefit and Net Increase in Grower Income", ISHS Acta Horticulturae, vol. 868, 2010, pp. 273-282.
Guardiola, "Increasing Citrus Fruit Size With Synthetic Auxins", Departamento de Biologia Vegetal, Universidad Politecnica de Valencia. Valencia. Spain, 1997, pp. 79-86.
Han et al., "A Novel Inhibitor of 9-cis-Epoxycarotenoid Dioxygenase in Abscisic Acid Biosynthesis in Higher Plants", Plant Physiology, vol. 135, Jul. 2004, pp. 1574-1582.
IFDC, "What are fertilizers?", Available online at: <http://www.ifdc.org/Media_Center/Fertilizer_FAQs/>, 2012, 5 pages.
International Preliminary Report on Patentability received for PCT Patent Application No. PCT/US2010/062267, dated Jul. 12, 2012, 6 pages.
International Preliminary Report on Patentability received for PCT Patent Application No. PCT/US2010/062268, dated Jul. 12, 2012; 5 pages.
International Search Report and Written Opinion received for PCT Patent Application No. PCT/US2010/062267, dated Sep. 20, 2011, 9 pages.
International Search Report and Written Opinion received for PCT Patent Application No. PCT/US2010/062268, dated Sep. 20, 2011, 8 pages.
Ito et al., "Studies on the Physiological Responses of Crop Plants following Application of Exogenous Nucleic Acid Components. I. Effect of Exogenous Nucleic Acid Components on the Germination of Seeds and the Growth of Seeding during the Early Stages of the Rice Plant, *Oryza stativa*", Database Accession No. 85:42078, May 12, 1984, 2 pages.
Jaganath et al., "Efficacy Studies on Prebloom Canopy Applications of Boron and/or Urea to 'Hass' Avocados in California", Proceedings of the World Avocado Congress III, 1995, pp. 181-184.
Khoshbakht et al., "How Many Plant Species are Cultivated?", Genet Resour. Crop, Evol., vol. 55, 2008, pp. 925-928.
Kobayashi et al., "Fruit-Setting and Fruit Enlargement Promoting Agent (Full Translation)", Translated by Phoenix Translations, Jan. 2014, pp. 1-8.
Kobayashi et al., "Growth Promoting Agents for Vegetables and Grains", Database Accession No. 80:44694, May 12, 1984, 2 pages.
Lovatt et al., "Developing Field Strategies to Correct Alternate Bearing", 2008 Production Research Report, Management and Physiology, California Avocado Commission, 2008, 6 pages.
Lovatt et al., "PGR Strategies to Increase Fruit Size of 'Hass' Avocado", 2008 Production Research Report, Management and Physiology, California Avocado Commission, 2008, 3 pages.
Lovatt et al., "PGR Strategies to Increase Yield of 'Hass' Avocado", 2008 Production Research Report, Management and Physiology, California Avocado Commission, 2008, 7 pages.
Lovatt et al., "UC I PM: Plant Growth Regulators in Citrus: General Information", available at <http://www.ipm.ucdavis.edu/PMG/r107900111.html>, accessed on Apr. 11, 2013, 3 pages.
Lovatt et al., "Urea Combined with 6-Benzyladenine to Reduce Alternate Bearing in Pistachio and to Increase Cumulative Yield", Extension Pomologist, Univ. of California, Davis/Kearny Agricultural Center, 2001, pp. 346-356.
Lovatt et al., "Improving the Efficacy of GA3 to Increase Fruit Set and Yield of Clementine Mandarins in California", 2007 Annual Report, Plant Management & Physiology, Citrus Research Board, 2007, pp. 9-17.
Lovatt, "Plant Growth Regulators for Avocado Production", California Avocado Society 2005 Yearbook, vol. 88:81-91, 2005, 7 pages.
Lovatt, "Timing Citrus and Avocado Foliar Nutrient Applications to Increase Fruit Set and Size", Hort Technology, vol. 9, No. 4, Oct.-Dec. 1999, pp, 607-612.
My Agriculture Information Bank, "Classification of Crop Plants", retrieved from Internet on Aug. 7, 2013 <http://agriinfo.in/?page=topic&superid=1&topicid=309>, 3 pages.
New Agriculturist, "Perennial Upland Rice Takes Root", retrieved from Internet on Aug. 8, 2013 <http://www.new-ag.info/en/developments/devItem.php?a=798>, 2 pages.
Rao et al., "Enhancement of polyribosome formation by gibberellic acid and 3',5'-adenosine monophosphate in barley embryos", Biochemical and Biophysical Research Communications. vol. 62, No. 1, 1975, pp. 25-30.
Ries et al., "9-β-L(+) Adenosine: A New Naturally Occurring Plant Growth Substance Elicited by Triacontanol in Rice", Plant Growth Regulation, vol. 9, No. 3, Aug. 1990,, pp. 263-273.
Ries, Stanley, "Triacontanol and Its Second Messenger 9-β-L(+)-Adenosine as Plant Growth Substances", Plant Physiol., vol. 95, 1991, pp. 986-989.
Sigma-Aldrich, "Adenosine-Material Safety Data Sheet", A9251, Version 5.0, 2012,6 pages.
Spinelli et al., "Perspectives on the Use of a Seaweed Extract to Moderate the Negative Effects of Alternate Bearing in Apple trees", Journal of Horticultural Science & Biotechnology, ISAFRUIT Special Issue 2009, pp. 131-137.
"The Growth Stages of the Rice Plant", International Rice Research Institute, Lesson 2, available online at <http://www.knowledgebank.irri.org/ericeproduction/0.2>, 2007, 2 pages.
Verreynne et al., "Citrus Fruit Reduce Summer and Fall Vegetative Shoot Growth and Return Bloom", Proceedings of the International Society of Citriculture, vol. II., Feb. 2004, pp. 520-524.
Verreynne et al., "The Effect of Crop Load on Budbreak Influences Return Bloom in Alternate Bearing 'Pixie' Mandarin", J. Amer. Soc. Hort. Sci., vol. 134, No. 3, 2009, pp. 299-307.
Verreynne, "The Mechanism and Underlying Physiology Perpetuating Alternate Bearing in 'Pixie' Mandarin (*Citrus reticulata* Blanco)", Pd.D. Thesis, University of California Riverside, Jun. 2005, 214 pages.
Woo et al., "Flavonoids: From Cell Cycle Regulation to Biotechnology", Biotechnology Letters, vol. 27, 2005, pp. 365-374.
"Fertilizers and Use", Food and Agriculture Organization of the United Nations, International Fertilizer Industry Association (IFA). 4th edition, 2000.
"Humic—Plant Nutrition", Product Catalogue—Amino acids. Datasheet of Briohumic, available at <http://www.humic.es/aminoacidos/briohumic.pdf>, Oct. 2007.
Ito et al., "Studies on the Physiological Responses of Crop Plants Following Application of Exogenous Nucleic Acid Components. I. Effect of Exogeneous Nucleic Acid Components on the Germination of Seeds and the Growth of Seeding During the Early Stages of the Rice", Plant, *Oryza stativa*, Tokyo Nogyo Daigaku Nogaku Shuho, vol. 20, No. 1, 1975, pp. 35-42.(Japanese with English Translation).
Tu et al., "Weed Control Methods Handbook: Tools & Techniques for Use in Natural Areas", The Nature Conservancy, Chapter 8—Adjuvants, 2001, pp. 8.1-8.25.
Wang et al., Effects of Plant Growth Regulators on Growth of Both Spanish-and Virginia-Type Peanut (*Arachis hypogaea* L), Weed Sci Bull, vol. 14, No. 2, 1993, pp. 137-148.

\* cited by examiner

FIGURE 1
Navel Orange

FIGURE 2

Hass Avocado

MITIGATION OF ALTERNATE BEARING

CROSS-REFERENCE TO RELATED APPLICATIONS

This application is a continuation of U.S. application Ser. No. 13/519,888, which is a national stage application of International Application No. PCT/US2010/062268, filed Dec. 28, 2010, which claims the benefit under 35 USC 119(e) of U.S. Provisional Application No. 61/290,470, filed Dec. 28, 2009, all of which are hereby incorporated herein by reference in their entirety for all purposes.

FIELD

Described are compositions and methods to mitigate alternate bearing of perennial crops by use of a natural metabolite. In particular, the present disclosure provides a natural metabolite in the presence or absence of an auxin transport inhibitor to increase floral intensity (flower number) of the return bloom in the spring following the setting of a heavy on-crop to increase the yield of the putative off-crop year and, thus, increase cumulative crop yield. Additionally the present disclosure provides a natural metabolite in combination with one or more of a growth promoting type of plant growth regulator, and a hormone biosynthesis, transport or function inhibiting type of plant growth regulator.

BACKGROUND

Alternate bearing (also called biennial or uneven bearing) is the tendency of a perennial crop plant to produce a heavy crop in one year (on-crop, on-year) followed by a light crop or no crop (off-crop, off-year). During the on-crop year, there is a high yield of small fruit with reduced market value, while during the off-crop year, the fruit size is good but there are too few fruit to provide the grower with a good income after covering production costs. This leads to price instability, erratic annual returns to growers, and possible loss of market share. The lack of crop in the off-crop year also compromises the development or sustainability of value-added products industries.

The alternate bearing phenomenon is widespread, occurring in both deciduous and evergreen trees, as well as in both perennial fruit and nut crops. It may occur over an entire region, in a block of trees, in an individual tree, or even in part of a tree or one branch. This problem is of significant economic consequence in apple, apricot, avocado, citrus, especially mandarin, peach, pecan, pistachio and plum to name a few crops of commercial value. Approximately every other year, grower income is reduced below the orchard's potential by production of an off-crop. Therefore, there is a recurring need to mitigate alternate bearing.

Alternate bearing is initiated by climatic conditions (e.g., freeze damage, lack of chilling, low or high temperatures during flowering or fruit set) that cause poor flowering or excessive flower or fruit drop, resulting in an off-crop. This is followed by an on-crop, typically the next year, depending on how long it takes for the trees to recover. Conversely, climatic conditions that are optimal for flowering and fruit set such that crop thinning fails to take place result in an on-crop that is followed by an off-crop. Once initiated, alternate bearing becomes entrained through the effect of crop load on endogenous tree factors that ultimately impact floral intensity, such that the heavy on-crop reduces return bloom the following spring, whereas the light off-crop results in an intense return bloom the next spring. Because alternate bearing is initiated by climate, the need for a corrective strategy is recurring.

Fruit is the main tree factor causing alternate bearing, and the number of fruit on a tree is the main factor influencing floral intensity of the return bloom. The presence of a large number of fruit (heavy on-crop) reduces the number and length of summer and fall vegetative shoots in a variety of perennial fruit and nut crops, thereby reducing number of shoots and nodes on shoots that can produce inflorescences in the spring (Verreynne, Ph.D. Thesis, University of California Riverside, 2005; and Verreynne and Lovatt, J Amer Soc Hort Sci, 134:299-307, 2009). The presence of a large number of fruit on the tree in spring also inhibits spring bud break, further reducing the number of floral shoots and flowers that develop in spring. In some crops the fruit is not mature and cannot be harvested until after spring bloom, but for others, the presence of the mature crop on the tree in spring unnecessarily increases the degree of alternate bearing (Verreynne, Ph.D. Thesis, University of California, Riverside, 2005; and Verreynne and Lovatt, J Amer Soc Hort Sci, 134:299-307, 2009).

Current strategies to mitigate alternate bearing require reducing production in the on-crop year. This may be accomplished by inhibiting flowering, or removing flowers or young fruit chemically, by pruning or by hand. As such, what is needed in the art are compositions and methods to mitigate alternate bearing that are safe without being labor intensive and that do not reduce yield in the on-crop year.

SUMMARY

Described are compositions and methods to mitigate alternate bearing of perennial crops by use of a natural metabolite. In particular, the present disclosure provides a natural metabolite (adenosine or the like) in the presence or absence of an auxin transport inhibitor (plant growth regulator or naturally occurring flavonoid) to increase floral intensity (flower number) of the return bloom in the spring following the setting of a heavy on-crop to increase the yield of the putative off-crop year and, thus, increase cumulative crop yield. Additionally the present disclosure provides a natural metabolite in combination with one or more of a growth promoting type of plant growth regulator, and a hormone biosynthesis, transport or function inhibiting type of plant growth regulator.

The present disclosure provides methods of mitigating alternate bearing in a perennial crop plant, comprising administering to the perennial crop plant a composition comprising an effective amount of a purified natural compound to mitigate alternate bearing, wherein the natural compound is selected from the group consisting of adenosine, an adenosine phosphate, inosine, an inosine phosphate, adenine, hypoxanthine, xanthine, and combinations thereof. In other embodiments, the natural compound is selected from the group consisting of uridine, uridine monophosphate, uridine diphosphate, uridine triphosphate, and uracil. In some preferred embodiments, the natural compound comprises 9-beta-D-adenosine. In some preferred embodiments, the natural compound comprises one or more of the group consisting of adenosine monophosphate, adenosine diphosphate, adenosine triphosphate, inosine, inosine monophosphate, inosine diphosphate, inosine triphosphate, adenine, hypoxanthine, and xanthine. In some particularly preferred embodiments, the composition further comprises a plant growth regulator selected from the group consisting of 6-benzylaminopurine, zeatin, zeatinriboside, kinetin, isopentenyladenine, isopentenyladenosine, 1-(2-chloro-4-pyridynl)-3-phenylurea, gibberellic acid, 6-benzyladenine, 6-benzyladenosine, 2,3,5-triiodobenzoic acid, DPX 1840, 9-hydroxyflorene-9-carboxylic acid, and naptalam (N-1-naphthylphthalamic acid), fluridone (1-methyl-3-phenyl-5-[3-trifluromethyl(phenyl)]-4-(1H)-pyridinone), abamine, 1-butanol and combinations thereof. In some preferred embodiments, the plant growth regulator is 2,3,5-triiodobenzoic acid. In additional embodiments, the composition further comprises a flavonoid or an isoflavonoid selected from the group consisting of naringenin, quercetin, formononetin, genistein, and combinations thereof. In other embodiments, the composition further comprises a fertilizer selected from the group consisting of nitrogen, potassium, magnesium, phosphorus, calcium, sulfur, iron, boron, chlorine, manganese, zinc, copper, molybdenum, nickel, silicon, selenium, cobalt, and combinations thereof. In preferred embodiments, the crop plant is selected from the group consisting of apricot, avocado, citrus (e.g., orange, lemon, grapefruit, tangerine, lime and citron), peach, pear, pecan, pistachio, and plum. The present disclosure provides embodiments in which the composition is administered by a technique selected from the group consisting of foliar spray, irrigation, and trunk injection. In some embodiments, the mitigation of alternate bearing comprises one or more of the following: an increase in floral shoot number per 100 nodes in the spring following setting of a heavy on-crop, as compared to untreated on-crop trees; an increase in fruit yield in one year following setting of a heavy on-crop, as compared to untreated on-crop trees; and an increase in cumulative fruit yield over a 2-year period as compared to untreated on-crop trees. In some preferred embodiments, the composition is administered at initiation of summer vegetative shoot growth and prior to spring bud break. For instance in California or similar climates, in some embodiments the composition is administered once or twice as follows: in June, June plus December, June plus January, or June plus February. In some embodiments the composition is administered once or twice as follows: in July, July plus December, July plus January, or July plus February. In some embodiments, the composition is administered to citrus trees when the crop is a maximum peel thickness. In some preferred embodiments, the composition is administered 90 days or more before harvest, preferably four, five or six months before harvest of a crop during an off-crop year.

Moreover the present disclosure provides compositions effective in mitigating alternate bearing in a perennial crop plant, comprising: (i) a purified natural compound, and (ii) an auxin transport inhibitor, wherein the natural compound is selected from the group consisting of adenosine, an adenosine phosphate, inosine, an inosine phosphate, adenine, hypoxanthine, xanthine, and combinations thereof. In other embodiments, the natural compound is selected from the group consisting of uridine, uridine monophosphate, uridine diphosphate, uridine triphosphate, and uracil. In some preferred embodiments, the natural compound comprises 9-beta-D-adenosine. In some preferred embodiments, the natural compound comprises one or more of the group consisting of adenosine monophosphate, adenosine diphosphate, adenosine triphosphate, inosine, inosine monophosphate, inosine diphosphate, inosine triphosphate, adenine, hypoxanthine, and xanthine. In some embodiments, the auxin transport inhibitor is a plant growth regulator selected from the group consisting of 2,3,5-triiodobenzoic acid, DPX 1840, 9-hydroxyflorene-9-carboxylic acid, and naptalam (N-1-naphthylphthalamic acid) and combinations thereof. In some preferred embodiments, the plant growth regulator is 2,3,5-triiodobenzoic acid. In other embodiments, the auxin transport inhibitor is a flavonoid or isoflavanoid selected from the group consisting of naringenin, quercetin, formononetin, genistein, and combinations thereof. In additional embodiments, the compositions further comprise a fertilizer. The fertilizer is supplied at an amount effective to support one or both of vegetative shoot growth once correlative inhibition is overcome, and floral shoot development, flower development and fruit set once inhibition of spring bud break is overcome. In some embodiments, the fertilizer is selected from the group consisting of nitrogen, potassium, magnesium, phosphorus, calcium, sulfur, iron, boron, chlorine, manganese, zinc, copper, molybdenum, nickel, selenium, silicon, cobalt, and combinations thereof. In some embodiments, the fertilizer is low-biuret urea. In preferred embodiments, low-biuret urea is supplied in an amount effective to support shoot growth, floral development and improve uptake of compounds by leaves and buds. In other embodiments, the fertilizer is disodium octaborate tetrahydrate. In preferred embodiments, the disodium octaborate tetrahydrate (e.g., SOLUBOR®, U.S. Borax, Inc.) is supplied in an amount effective to increase spring bud break to increase pollen germination, pollen tube growth, fertilization and fruit set of seeded crops such as avocado, peach and pistachio.

Additionally the present disclosure provides compositions effective in mitigating alternate bearing in a crop plant, comprising: (i) a purified natural compound, and (ii) a plant growth regulator, wherein the natural compound is selected from the group consisting of adenosine, an adenosine phosphate, inosine, an inosine phosphate, adenine, hypoxanthine, xanthine, and combinations thereof. In other embodiments, the natural compound is selected from the group consisting of uridine, uridine monophosphate, uridine diphosphate, uridine triphosphate, and uracil. In some preferred embodiments, the natural compound comprises 9-beta-D-adenosine. In some preferred embodiments, the natural compound comprises one or more of the group consisting of adenosine monophosphate, adenosine diphosphate, adenosine triphosphate, inosine, inosine monophosphate, inosine diphosphate, inosine triphosphate, adenine, hypoxanthine, and xanthine. In some embodiments, the plant growth regulator is a growth promoting agent selected from the group consisting of 6-benzylaminopurine, zeatin, zeatin riboside, kinetin, isopentenyladenine, isopentenyladenosine, 1-(2-chloro-4-pyridynl)-3-phenylurea, gibberellic acid, 6-benzyladenine, and 6-benzyladenosine. In some embodiments, the plant growth regulator is applied in an amount effective to achieve a synergistic effect on bud break. In other embodiments, the plant growth regulator is an inhibitor of abscisic acid biosynthesis or abscisic acid function selected from the group consisting of fluridone, abamine, and 1-butanol. Also the present disclosure provides compositions further comprising a fertilizer selected from the group consisting of nitrogen, potassium, magnesium, phosphorus, calcium, sulfur, iron, boron, chlorine, manganese, zinc, copper, molybdenum, nickel, selenium, silicon, cobalt, and combinations thereof.

BRIEF DESCRIPTION OF THE DRAWINGS

FIG. 1 is a timeline depicting the flowering, fruit set and fruit development of the Navel orange over a one-year period. Trees transition from vegetative to reproductive (floral) development from late November through January, with irreversible commitment to flowering (determinancy) occurring between mid-December and mid-January. Flowering and flower abscission may occur between February and mid-May or June. Fruit set may occur between February and July. Fruit abscission may occur between April and August. Fruit development unfolds in three stages. During Stage I, which may occur between February and July, fruit size slowly increases. The end of Stage one is marked by maximum thickness of the peel and has been experimentally shown to occur between approximately June 10 and July 26 for both navel and Valencia orange and mandarins from as far south as Irvine Calif. north to Madera Calif., occurring earlier within this period for cultivars with a thinner peel, i.e., mandarin<Valencia<navel and earlier within a cultivar during an on-crop year than an off-crop year. During Stage II, which may occur between June and November, fruit size rapidly increases. During Stage III, which may occur between November and January of the following year, is a maturation stage wherein the increase in fruit size slows down again. Stages I and II (early fruit drop and June fruit drop period, respectively) are the critical period for fruit retention and increasing yield. The end of Stage I through Stage II is the critical period for increasing fruit size. Pre-harvest may occur between September and December, while harvest may occur from December until as late as June of the following year. FIG. 1 is based on 25-year-old 'Washington' navel orange trees on Troyer citrange rootstock at Riverside, Calif.

FIG. 2 is a timeline depicting the flowering, fruit set and fruit development of the 'Hass' avocado in California over approximately a 1.5-year period. The 'Hass' avocado in California transitions from vegetative to reproduction development (inflorescence initiation) at the end of July beginning of August. Flower initiation may occur from November to January of the following year. Flowering may occur between March and May. Pollination and fertilization may occur between March and June. Fruit set may occur between March and mid-June to early July. Early fruit drop may occur between March and mid-June to early July; June drop occurs from mid-June to early July through August. Fruit development unfolds in three stages. During Stage I, which may occur between April and mid-June-early July, fruit size slowly increases. During Stage II, which may occur between mid-June-early July through November, fruit size rapidly increases. During Stage III, the fruit continue to undergo cell division and to accumulate dry matter and oil content as part of maturation, which continues through harvest (20.8% dry matter content is legal maturity) the following year. The critical period for fruit retention and increasing yield is between March and August. The critical period for increasing fruit size is mid-June to early July through November and again late March to early April through to harvest the following year. Harvest may occur between February until fall, wherein the main pick occurs between May and July. FIG. 2 is based on San Diego-Riverside environmental conditions.

DEFINITIONS

Figure 1:
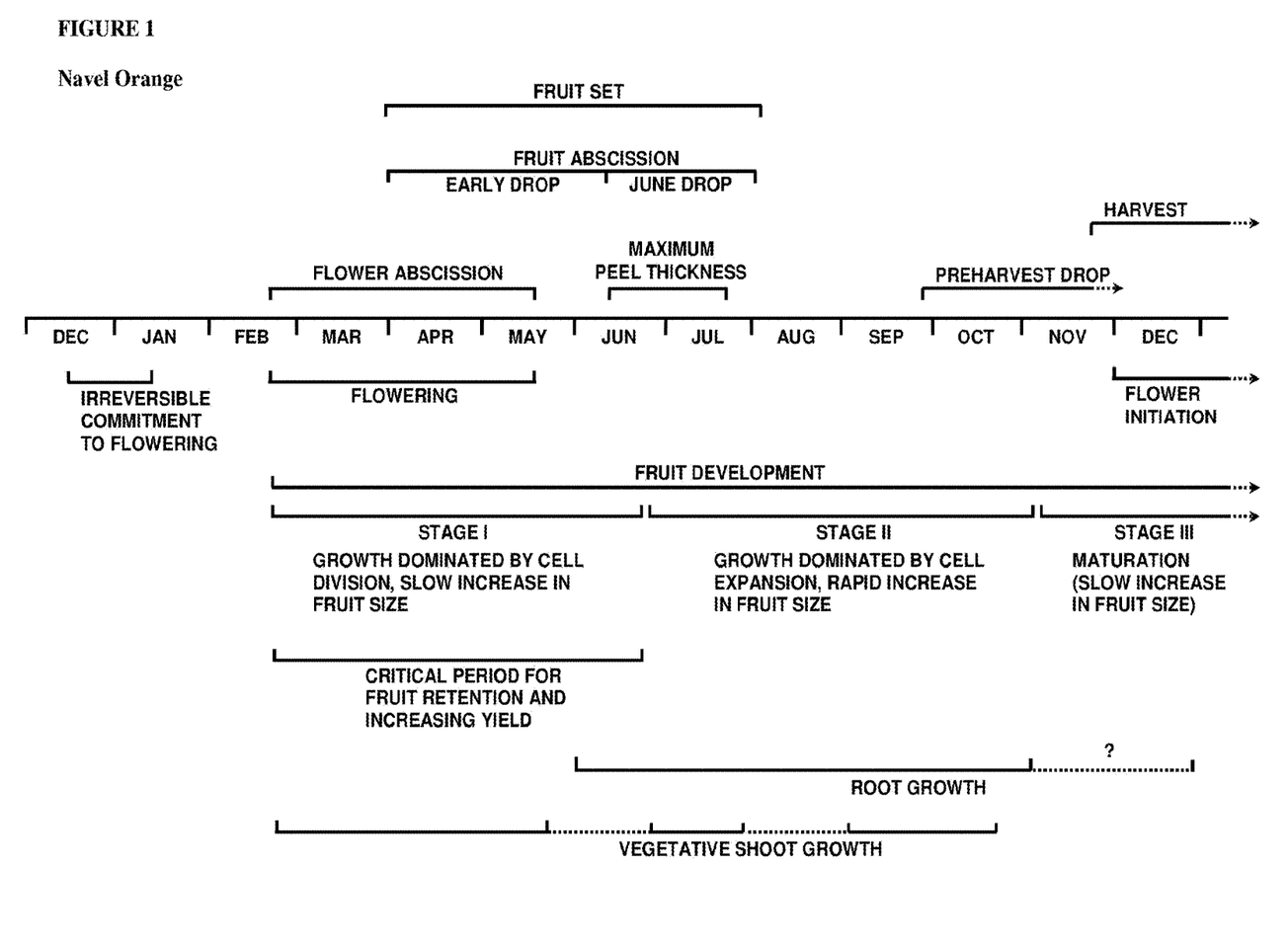
Figure 2:
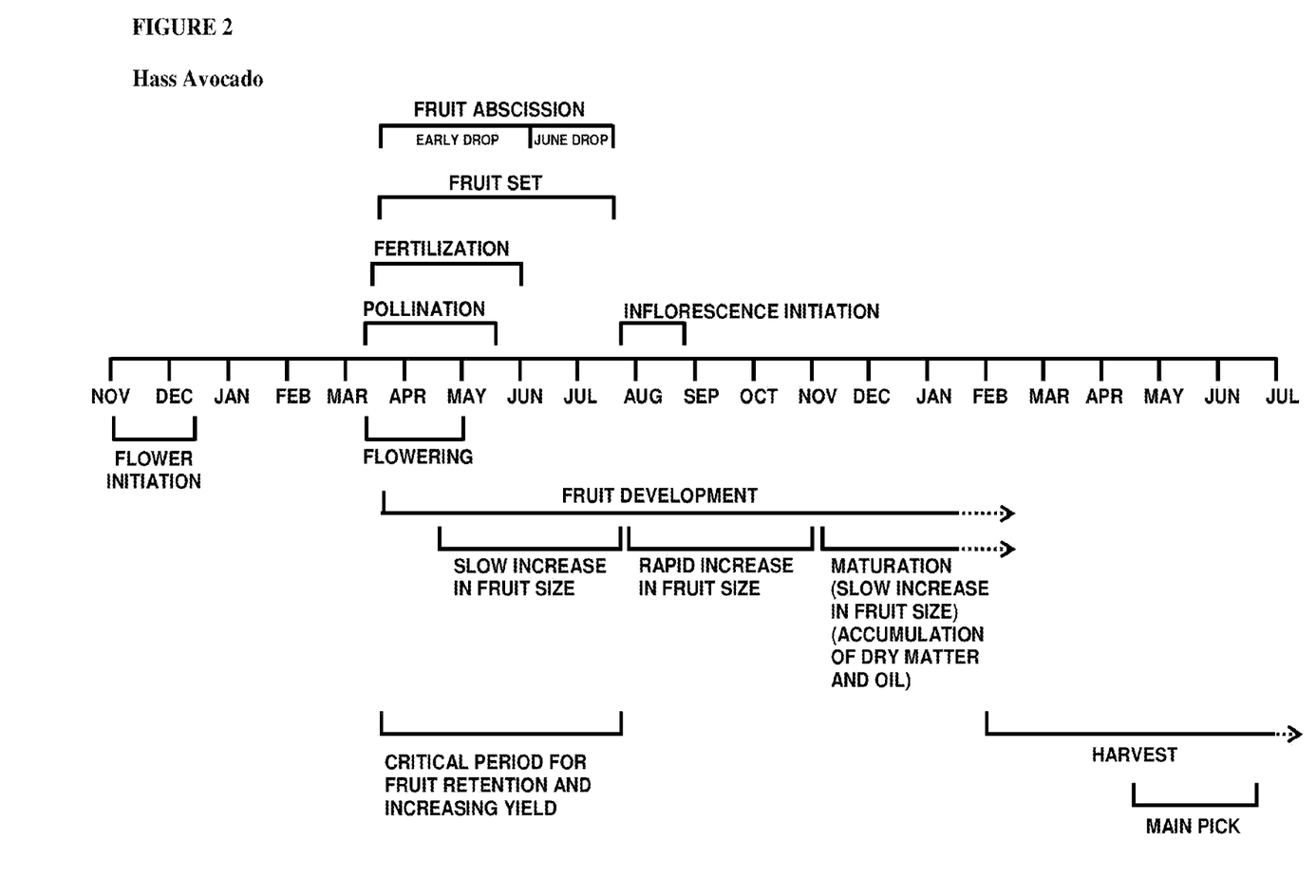

To ensure a complete understanding of this disclosure, the following definitions are provided.

The term "mitigating alternate bearing" as used herein refers to an increase in floral shoot number and flower number in the spring of the year following the setting of a heavy on-crop resulting in an increase in crop yield in the year following the heavy on-crop year (putative off-crop year) to achieve an increase in cumulative yield over that of a tree or orchard left untreated and over that of a tree or orchard for which crop load was reduced in the on-crop year, (current standard practice for mitigating alternate bearing).

The present disclosure overcomes the effect of the high number of fruit in the on-crop year to stimulate bud break to increase flowering in two steps; each step can be used alone or in combination to control the degree of return flowering. The two steps are: (1) to overcome the inhibition of bud break to increase the amount of summer shoot growth to increase the number of nodes and floral bud development at those nodes to increase the number of floral shoots in spring; and (2) to stimulate floral bud break in spring on the summer (and also spring) flush shoots. This will increase yield over trees not treated with this technology because yield is proportional to flower number. Alternatively, mitigation of alternate bearing is enumerated as a measurable increase in two-year cumulative yield compared to an untreated control.

The term "crop yield" as used herein refers to growth of flowers, fruits, seeds. As such an increase in crop yield refers to an increase in one or both of the size and quantity of the reproductive organs of a plant, including but not limited to fruit, seeds/nuts, and flowers. The term "size" as used herein refers to the weight, length, area, diameter, circumference or volume of a reproductive organ, while the term "quantity" as used herein refers to number of reproductive organs. An increase in size encompasses an increase in fruit size (e.g., diameter, circumference, volume, weight). In preferred embodiments, the increase in crop yield is a net increase of at least 10%, 20%, 30%, 40%, 50%, 75%, 85%, 95%, 100%, 150%, 200% in fruit production (e.g., number of fruit [total, large, or commercially valuable] per crop plant, weight of fruit [total, large, or commercially valuable] per crop plant, or total yield of fruit per crop plant) as compared to the respective values of untreated control plants. Crop yield is generally expressed in: total kilograms of fruit per crop plant, average kilogram per fruit per crop plant, total number of fruit per crop plant, average number of fruit per crop plant, average millimeters in diameter per fruit, or in average grams per fruit.

The term "total yield" as used herein refers to the product of size multiplied by quantity of a plant organ. In preferred embodiments, the increase in total yield is a net increase of at least 10%, 20%, 30%, 40%, 50%, 75%, 100%, 150%, 200%, 250%, 300%, 350%, 400%, or 500% of the total yield of one or both of vegetative and reproductive growth as compared to the value of untreated control plants.

The term "administer" as used herein refers to various ways in which a crop plant receives the compositions described herein (e.g. nutritional supplements, plant growth regulators, fertilizers or combinations thereof). Methods of administration include, but are not limited to trunk injection (including branch injection), trunk paints (including branch paints), foliar spray, irrigation, and soil injection (or soil spray).

Trunk injection involves directly administering the composition to the plant. As known in the art, trunk injection is a way to treat many different insect and disease problems, as well as nutrient deficiencies, in an efficient and environmentally friendly way. Also, some trees are too large to spray, in areas too close to houses, parks, water courses, or other environmentally sensitive areas where spraying is not a viable option, or the root system may be inaccessible for soil systemic treatments, making trunk injection the best or only option available in such cases. Foliar spraying, a different technique of feeding plants, involves directly applying the composition in liquid form to the canopy of the plant. Whereas foliar sprays typically target a plant's leaves, other organs such as buds, flowers, inflorescences, shoots and fruit may be the target of these applications. In contrast, irrigation, soil application, soil injection, soil sprays involve directly administering the composition (as a liquid or dissolvable solid material) to the soil for uptake by the plant roots.

The term "effective amount" as used herein refers to that amount of a substance necessary to produce a desired effect. For example, an effective amount of adenosine is that amount of adenosine that mitigates alternate bearing when the adenosine is administered to a suitable crop plant. Typically, an effective amount of adenosine administered to a crop plant by trunk injection is between 100 mg to 2 g per tree per application. A preferred effective amount of adenosine by trunk injection is about 500 mg to 1 g per tree with 1 or 2 applications. Typically, an effective amount of adenosine administered to a crop plant by foliar spray is 25 mg/L to 100 mg/L applied in 100 to 500 gallons of water per acre. A preferred effective amount of adenosine is about 25 or 50 mg/L applied as a foliar spray in 200 or 250 gallons of water per acre.

Typically, an effective amount of 2,3,5-triiodobenzoic acid (TIBA) administered to a crop plant by trunk injection is between 100 mg to 1 g per tree per application. A preferred effective amount of TIBA by trunk injection is about 500 mg to 1 g per tree with 1 or 2 applications. Typically, an effective amount of TIBA administered to a crop plant by foliar spray is 25 mg/L to 100 mg/L applied in 100 to 500 gallons of water per acre. A preferred effective amount of TIBA is about 25 or 50 mg/L applied as a foliar spray in 200 or 250 gallons of water per acre.

The term "natural metabolite" as used herein refers to a substance existing in nature that is involved in metabolism (e.g., product of or necessary for metabolism). In some embodiments, the natural metabolite is adenosine. Similarly, the term "natural compound" as used herein refers to a substance existing in nature, albeit whether the isolated compound is produced biologically or chemically. For the sake of simplicity, the terms "natural metabolite" and "natural compound" are used interchangeably herein. In some preferred embodiments the natural compound is: a purine nucleoside (e.g., adenosine, inosine); a monophosphate, diphosphate or triphosphate of a purine nucleoside (e.g., AMP, ADP, ATP, IMP, IDP, ITP); or a purine base (e.g., adenine, hypoxanthine, xanthine). In preferred embodiments, the natural metabolite comprises adenosine. In preferred embodiments, the purine nucleoside comprises or consists essentially of the D stereoisomer (e.g., 9-beta-D-adenosine, 9-beta-D-inosine).

As used herein, the term "purified" refers to a metabolite (e.g., adenosine or the like) that is removed from its natural environment (e.g., isolated or separated). "Purified" compounds are at least 50% free, preferably 75% free, more preferably at least 90% free, and most preferably at least 95% (e.g., 95%, 96%, 97%, 98%, or 99%) free from other components with which they are naturally associated.

The term "nutritional supplement" as used herein refers to a composition comprising one or more basal metabolites needed for normal growth of plants, and which are in a form readily useable by plants. In some preferred embodiments, the nutritional supplement comprises the natural metabolite adenosine, which in some preferred embodiments is 9-beta-D-adenosine. In other preferred embodiments the nutritional supplement comprises the natural metabolite adenosine in combination with pyrimidine nucleosides, bases or nucleotides, amino acids, organic acids, anti-oxidants, sugars and vitamins, enzyme cofactors.

The term "plant growth regulator" as used herein refers to a synthetic chemical compound analog of a naturally occurring plant hormone that is applied to mimic the effects of plant hormones. The naturally occurring plant hormones generally fall under one of five classes: auxin, gibberellin (GA), cytokinin, ethylene, and abscisic acid (ABA). Plant growth regulators include but are not limited to 2,3,5-triiodobenzoic acid (TIBA); 9-hydroxyflorene-9-carboxylic acid (HFCA); 2-(4-chlorophenoxy)-2-methylpropionic acid (clofibric acid); 4-chlorophenoxyacetic acid (4-CPA); 2,4-dichlorophenoxyacetic acid (2,4-D); 2,4,5-trichlorophenoxyacetic acid (2,4,5-T); 3,5,6-trichloro-2-pyridyloxyacetic acid (3,5,6-TPA); 4-(2,4-dichlorophenoxy)butyric acid (2,4-DB); tris[2-(2,4-dichlorophenoxy)ethyl]phosphite (2,4-DEP); 2-(2,4-dichlorophenoxy)propionic acid (dichlorprop); 2-(2,4,5-trichlorophenoxy)propionic acid (fenoprop); 1-naphthaleneacetic acid (NAA); indole-3-butyric acid (IBA); indole-3-acetic acid (IAA); 4-chloroindole-3-acetic acid (4-CI-IAA); 2-phenylacetic acid (PAA); 2-methoxy-3,6-dichlorobenzoic acid (dicamba); 4-amino-3,5,6-trichloropicolinic acid (tordon or picloram); α-(p-Chlorophenoxy)isobutyric acid (PCIB); 1-naphthol; (2-naphthyloxy)acetic acid; potassium naphthenate; sodium naphthenate; N-(3-methylbut-2-enyl)-1H-purin-6-amine (2iP); N-benzyl-1H-purin-6-amine (benzyladenine); N-furfuryl-1H-purin-6-amine (kinetin); (E)-2-methyl-4-(9H-purin-6-ylamino)but-2-en-1-ol (zeatin and its riboside); 6-benzylaminopurine (6BA and its riboside); isopentenyladenine and its riboside; 1-(2-chloro-4-pyridynl)-3-phenylurea (CPPU), forchlorfenuron, and other synthetic diphenylurea-type cytokinins; cis, trans-abscisic acid; S-(+)-abscisic acid; (S)-5-(1-hydroxy-2,6,6-trimethyl-4-oxo-1-cyclohex-2-enyl)-3-methyl-penta-(2Z,4E)-dienoic acid; and gibberellic acids ($GA_3$, $GA_4$, $GA_7$, $GA_{4+7}$, $GA_9$, $GA_{4,7,9}$, $GA_1$), fluridone (1-methyl-3-phenyl-5-[3-trifluromethyl(phenyl)]-4-(1H)-pyridinone), aminoethoxyvinylglycine, ethrel and ethephon.

The term "auxin transport modulator" as used herein refers to a compound that modulates the movement of auxin from one part of the plant to another and affects plant growth. Auxin transport modulators include auxin transport inhibitors, which inhibit the movement of auxin. Examples of synthetic auxin transport inhibitors include, but are not limited to the herbicides 2,3,5-triiodobenzoic acid (TIBA), DPX 1840, 9-hydroxyflorene-9-carboxylic acid, and naptalam (N-1-naphthylphthalamic acid). In other embodiments the present disclosure provides natural auxin transport inhibitors. Naturally-occurring auxin transport inhibitors include the isoflavonoids formononetin and genistein, and the flavonoids quercetin and naringenin.

The term "fertilizer" as used herein refers to one or more of the 17 nutritional elements essential for plant, including fruit growth, and any of several elements shown to be beneficial to plant growth. Fertilizers may be added to the soil of crops, as liquids or solids, for uptake by plant roots (e.g. soil-applied, irrigation-applied) or applied to the canopy of the tree for uptake through leaves, flowers, fruit, shoots and buds. Fertilizers may be organic (i.e. composed of decayed plant or animal matter) or inorganic (i.e. composed of single or multiple chemicals and minerals). Fertilizers may include, in varying proportions, the essential elements: nitrogen, phosphorus, potassium, calcium, sulfur, magnesium, boron, chlorine, manganese, iron, zinc, copper, molybdenum, and nickel. Fertilizers may also include the beneficial elements cobalt, silicon, selenium, and chromium. Urea (e.g. low-biuret urea) is an example of a preferred nitrogen fertilizer because of its ability to facilitate uptake of compounds by plant tissues.

The term "biostimulant" as used herein refers to a compound or composition that is neither a fertilizer nor pesticide, but which when applied to a plant will enhance the health and growth of a plant. The term biostimulant encompasses but is not limited to amino acids, organic acids, nucleic acids, nucleotides, nucleosides and bases, sugars, vitamins, enzyme cofactors, humic acid, fulvic acid, kelp (seaweed), and compost tea.

The term "canopy" as used herein refers to any or all of the components of a plant that are above the level of the soil except the trunk. As such, the canopy consists of, but is not limited to branches, leaves, inflorescences, flowers, buds and fruit.

The term "crop plant" as used herein generally refers to cereal, legumes, forage crops, stem and leaf crops, root crops, fruit and seed vegetables, fruit and nut crops, beverage crops, oil, fat and wax crops, spices, perfumes and flavorings, and ornamentals, forest and fiber crops.

The term "crop plant" may refer to perennials, biennials or annuals. A perennial plant lives for more than two years. In contrast, an annual plant germinates, flowers, and dies in one year; a biennial plant completes its life cycle in two years. The embodiments in this disclosure are directed towards perennial crops.

Perennial crop plants include but are not limited to grapes, strawberries, walnuts, pistachios, citrus (navel, valencia, mandarin [tangerine], grapefruit, pummelo, lemons, limes, tangelos, kumquats), avocados, bushberries, peaches, plums, nectarines, cherries, plums, apricots, peaches, pears, pecans, apples, mangos, and almonds. The term "perennial crop plant" also encompasses cane crops (e.g., raspberries) and ornamentals (e.g., roses).

DETAILED DESCRIPTION

Alternate bearing occurs when a crop plant produces a heavy crop one year (on-crop, on-year) followed by a light crop or no crop (off-crop, off-year). This phenomenon is quantified as shown in Table I below:

TABLE I

Alternate Bearing Occurring in Fruit Orchards

|  | On-Crop (kg fruit/tree) | Off-Crop (kg fruit/tree) |
| --- | --- | --- |
| Orchard #1 | 134 | 47 |
| Orchard #2 | 187 | 61 |
| Orchard #3 | 80 | 18 |

The present disclosure provides a solution to the problem of alternate bearing in perennial crops that embodies use of a natural compound in the presence or absence of an auxin transport modulator (inhibitor). In some embodiments, the natural compound is provided in combination with one or more of a fertilizer and a plant growth regulator (e.g., growth promoting type, and/or biosynthesis, transport and function inhibiting type). The terms natural compound and natural metabolite are used interchangeably herein. In some embodiments, the natural metabolite comprises one or more of adenosine, adenosine phosphates (AMP, ADP, ATP) inosine, inosine phosphates (IMP, IDP, ITP) adenine, hypoxanthine, and xanthine. In some preferred embodiments the natural metabolite comprises adenosine. In some preferred embodiments, adenosine comprises or consists essentially of the D stereoisomer (e.g., 9-beta-D-adenosine). In the detailed description below, exemplary methods and compositions comprising 9-beta-D-adenosine are provided. However, the present disclosure is not so limited and as such other suitable compositions and methods for mitigation of alternate bearing comprise adenosine phosphates, inosine, inosine phosphates, adenine, hypoxanthine and xanthine in addition to or instead of adenosine.

Adenosine is unique as a natural metabolite precursor of such important components of all living cells and organisms as DNA, RNA, and ATP (the energy currency of all living cells and organisms) and of cytokinins in plants. Thus, adenosine is well suited to overcome the negative effects exerted by the high number of fruit in the on-crop year on inhibition of bud break due to high auxin and low cytokinin content (correlative inhibition) in summer and inhibition of bud break due to high abscisic acid and low cytokinin content and reduced carbohydrate availability in spring.

A. Hormone Basis for on- and Off-Crop Cycles

Results of research on 'Pixie' mandarin (Citrus reticulata) in Ojai, Calif., provide strong evidence that the high number of young fruit developing during an on-crop year inhibit bud break of the buds that would have developed into the summer and fall vegetative shoots, thus reducing the number shoots and the number of nodes (sites) on shoots that can produce floral buds and inflorescences the following spring (Verreynne, Ph.D. Thesis, University of California, Riverside, 2005; and Verreynne and Lovatt, J Amer Soc Hort Sci, 134:299-307, 2009). Detailed studies quantifying the effects of removing young fruit on floral intensity, vegetative shoot number and the number of inactive buds the next spring, confirmed that the summer flush shoots are essential for a good return bloom. Further, fruit removal research provided evidence that (i) young developing fruit of an on-crop and (ii) the mature fruit of an on-crop left on the trees through spring (as is the case for late-harvested citrus cultivars, including cultivars of mandarin, navel and Valencia) contribute significantly to alternate bearing by inhibiting spring bud break.

Young Developing Fruit Inhibit Summer Shoot Development.

The inhibition of summer shoot development is due to correlative inhibition, which involves high concentrations of the hormone indole-3-acetic acid (IAA), an auxin, and low concentrations of the cytokinin isopentenyladenosine (IPA) in the buds (Verreynne, Ph.D. Thesis, University of California, Riverside, 2005). The fruit export IAA, which accumulates in the buds for the summer flush shoots. In an on-crop year, bud concentrations of IAA are high and many buds are affected. Concurrently, root-produced cytokinins moving to the scion (canopy) of the tree in the xylem are diverted into the fruit and do not reach the buds for summer flush shoots. In an on-crop year, there are many fruit to divert the cytokinins. The result is a high auxin to low cytokinin ratio and correlative inhibition of the buds, reduced summer (and fall) vegetative shoot number, reduced floral bud development and reduced flowering the next spring. Removal of fruit in July eliminates the source of IAA and allows the cytokinins to reach the buds, which results in the growth of the summer and fall flush shoots, development of floral buds and a high number of inflorescences and flowers the next spring that set a high number of fruit and produce a high yield. Analysis of fruit exudates confirmed that fruit were the source of IAA. The removal of all fruit in July from on-crop trees decreased shoot IAA from 452 ng/g DW to 179 ng/g DW (P=0.0091) and increased shoot IPA concentrations from 50 ng/g DW to 118 ng/g DW (P=0.0537) equal to off-crop trees by August, and increased the number of SF shoots that developed and floral intensity at return bloom. The effect of low fruit number in the off-crop year is similar to the effect of fruit removal.

Contribution to Alternate Bearing of Mature Fruit of an On-Crop Left on the Trees Through Spring.

For late maturing cultivars like the 'Pixie' mandarin, the presence of nearly mature fruit on the tree in spring causes inhibition of spring bud break. In this case, inhibition of bud break is due to the accumulation of IAA and the accumulation of abscisic acid (ABA) exported by the fruit and the low amount of the cytokinin (IPA) reaching the buds. Fruit removal confirmed that fruit were the source of IAA and ABA and the reason IPA did not reach the buds. December fruit removal from on-crop trees decreased bud IAA and increased bud IPA concentrations by January and significantly increased return bloom. Fruit removal in February reduced the ratio of ABA:IPA to that off-crop trees by early March. Mature fruit of other cultivars that are left on the tree also cause inhibition of spring bud break. As determined during development of the present disclosure, high IAA and high ABA to low cytokinin ratios not only influences bud break, but also the expression of floral pathway genes. Since using the technology disclosed herein to reduce the IAA concentration and/or increase the cytokinin concentration of buds to reduce the IAA:cytokine ratio and ABA:cytoknin ratio increases floral intensity (both floral shoot and flower number), it follows that the technology also has a positive effect on regulating floral gene expression, as well as increasing bud break.

Conclusions.

The results of the fruit removal experiments, thus identified when fruit were exerting their negative effect and, hence, when corrective actions should be taken. Analysis of the buds collected in the fruit removal experiment for changes in hormone concentration revealed the role that hormones played in inhibition of bud break. Inhibition of bud break for summer and fall flush vegetative shoots resulted from export of indole-3-acetic acid (auxin) from the fruit and its accumulation in the buds, creating a high auxin to low cytokinin ratio (correlative inhibition), similarly inhibition of bud break in spring was due to high IAA and high abscisic acid to low cytokinin concentration in the buds. As such the methods and compositions of the present disclosure, which address one or both of inhibition of spring bud break due to a high IAA and high abscisic acid to cytokinin ratio, and correlative inhibition due to a high indole-3-acetic acid to cytokinin ratio, are suitable for mitigating alternate bearing in perennial crop plants. In both cases the results are in stark contrast to long-held paradigm that alternate bearing is the result of the heavy on-crop depleting the crop plant of carbohydrate reserves (energy) necessary to support floral development following the heavy on-crop year.

Extrapolation Beyond Citrus.

Research results with avocado (*Persea americana* cv. Hass) provide strong evidence that the two hormone-based mechanisms contributing to alternate bearing in the 'Pixie' mandarin are also the basis for alternate bearing in the 'Hass' avocado (Lovatt, 2008 Production Research Report of the California Avocado Commission, www.avocado.org/growers/symposiumcontent.php?research=m2). Moreover, in pistachio (*Pistacia vera* cv. Kerman), it is highly likely that the on-crop reduces the number and/or length of the summer vegetative shoots that bear next year's floral buds, resulting in a reduced number of floral buds for next year's crop. Results of earlier hormone analyses suggest that inhibition of summer shoot growth is due to correlative inhibition (high auxin to low cytokinin concentration). Thus, pistachio trees would benefit from a technology that increases bud break of the buds for the summer vegetative shoots and increases shoot length to increase the number of nodes (sites) at which floral buds are produced to increase return bloom in spring and thus to increase yield in the year following the on-crop year. Whereas pistachio is harvested in September, which might eliminate the need for the late winter treatment to mitigate alternate bearing, spring bud break might be enhanced by a late winter treatment to mitigate the increase in IAA and the high abscisic acid to low cytokinin ratio that develops in floral buds during the period of embryo development (nut fill) during the summer (Lovatt and Ferguson, Calif. Pistachio Industry Annual Rep. Crop: 114-115, 2002).

B. Methods for Mitigation of Alternate Bearing

The present disclosure embodies the use of a natural compound (adenosine or the like) in the presence or absence of an auxin transport inhibitor to mitigate the effect of the on-crop. Mitigation of the effect of the on-crop is accomplished by one or both of: (i) overcoming the inhibition of bud break of the buds for the summer shoot flush caused by the accumulation of auxin and reduction in cytokinin concentration (correlative inhibition); and (ii) overcoming the inhibition of spring bud break of floral buds caused by the accumulation of IAA and abscisic acid and reduced cytokinin concentration.

The present disclosure provides methods of mitigating alternate bearing in a perennial crop plant by administering to the crop plant a composition comprising an effective amount of adenosine (or the like). In some preferred embodiments, adenosine is administered alone or with an auxin transport inhibitor in early summer and late winter or early spring to overcome inhibition of summer and spring bud break, respectively. In some embodiments, the auxin transport inhibitor is a plant growth regulator (PGR) such as 2,3,5-triiodobenzoic acid (TIBA). In another embodiment, an auxin transport inhibitor, such as TIBA, is administered alone.

In another embodiment, the present disclosure employs 6-benzyladenine (6-BA) and TIBA. In another embodiment, the present disclosure employs isopentenyladenine (IPA) or isopentyladenosine (IPAdo) and TIBA. In other preferred embodiments, adenosine is administered with a naturally-occurring auxin transport inhibitor, such as quercetin or naringenin. In another embodiment, the present disclosure employs adenosine or the like in combination with a growth promoting (e.g., 6-BA, IPA, IPAdo, gibberellic acid) type of PGR to obtain a synergistic effect in overcoming alternate bearing. In another embodiment, the disclosure employs adenosine or the like in combination with an inhibitor of abscisic acid biosynthesis (e.g., fluridone) or abscisic acid function. In yet another embodiment, the present disclosure further employs low-biuret urea (or other fertilizer) to support increased shoot growth and improve uptake of compounds by leaves and buds.

The present disclosure has commercial potential for multiple reasons. First, the present disclosure provides a solution to the problem of alternate bearing for a number of commercially important fruit and nut crops. Second, the present disclosure is superior to current methods for mitigating alternate bearing because current methods require reducing on-crop yield. Third, the present disclosure provides a new use of a naturally occurring ubiquitous metabolite (adenosine or the like). Adenosine (or adenine) is a precursor of plant cytokinins, but is also a precursor for the synthesis of DNA, RNA and ATP and, thus, may properly be classified as a nutritional supplement instead of a PGR. In this way, the present disclosure provides formulations and methods for use by organic growers, who have access to few growth enhancers.

Previous investigators have shown that administration of AMP to cotton seed was effective in increasing seed germination (U.S. Pat. No. 4,209,316). In contrast, the present disclosure does not increase crop production as a consequence of enhancing seed germination. Moreover in preferred embodiments, the present disclosure comprises the administration of adenosine, as opposed to AMP.

The use of 1-tricontanol or 9-beta-L-adenosine has been reported to improve the quality of a harvested plant part (U.S. Pat. No. 5,217,738). In some instances this involved increasing the sugar to acid ratio of a harvested fruit or vegetable. In further reports, 9-beta-L-adenosine was administered to seedlings to increase dry weight or to plants once within 60 days of fruit or vegetable harvest to improve firmness or storage stability (U.S. Pat. Nos. 5,009,698 and 5,234,898). In contrast, the present disclosure involves the administration of a composition comprising a natural metabolite (adenosine or the like, preferably 9-beta-D-adenosine) to a perennial crop plant at a specific stage of crop phenology for the purpose of increasing flowering the next spring, an application unrelated to harvest and the postharvest quality of the fruit or vegetable. Moreover, the present disclosure involves increasing fruit and nut crop production (one or both of quantity and mass) in the putative off-crop year and over multiple growing seasons by the mitigation of alternate bearing. In preferred embodiments, the present disclosure involves administration of the natural metabolite to mitigate the inhibitory effect of the fruit on the specific physiological process of bud break and/or administration at a defined stage(s) of plant growth (planet phenology). As such the compositions and methods of the present disclosure differ significantly from the patents referred to above.

C. Compositions for Mitigation of Alternate Bearing

The present disclosure provides compositions to mitigate alternate bearing, comprising (i) adenosine (or the like) and (ii) an auxin transport inhibitor. In some embodiments, the auxin transport inhibitor is a plant growth regulator (PGR). In other embodiments, the auxin transport inhibitor is a flavonoid or an isoflavanoid. The present disclosure also provides compositions to mitigate alternate bearing comprising (i) adenosine (or the like) and (ii) a PGR. In some embodiments the PGR promotes plant growth or inhibits absicic acid synthesis, transport or function. In some embodiments, the compositions comprise a fertilizer. In some embodiments, mitigation of alternate bearing comprises an increase in the quantity and size of commercially valuable fruit in an alternate bearing orchard.

At present, there are only two PGRs registered for use on mandarins in California, gibberellic acid ($GA_3$) for increasing fruit set (retention of young fruit) and 2,4-dichlorophenoxyacetic acid (2,4-D) for increasing fruit size (University of California Pest Management Guidelines, www.ipm.ucdavis.edu/PMG/r107900111.html). Additionally, these PGRs are registered for use on other citrus to reduce preharvest drop (2,4-D) and prevent rind senescence ($GA_3$), while naphthalene acetic acid is registered for use on non-bearing citrus. Results of recent research (Chao and Lovatt, Final Report to the Citrus Research Board, 2007) provided evidence that $GA_3$ efficacy is impacted by alternate bearing. In the light crop year (approximately 550 fruit per tree), it was beneficial to apply $GA_3$ early (starting at 60% bloom), frequently (four applications) and at a higher rate (15 or 25 mg $GA_3$/L) to successfully increase the total number of fruit per tree, but not total yield as kilograms fruit per tree, and to increase the yield of commercially valuable large size fruit (packing carton sizes large, jumbo and mammoth) as both kilograms and number per tree. In the on-crop year (approximately 1200 fruit per tree), it was better not to apply $GA_3$. In the on-crop years in the study, $GA_3$ treatments either reduced both total yield and yield of commercially valuable large size fruit (packing carton sizes large, jumbo and mammoth) or had no effect. Use of 2,4-D to increase fruit size of mandarins carries the caution that it can cause fruit dryness in mandarin and mandarin hybrids. This is of particular concern for 'Nules' Clementine, which tends to have a low juice content, or in orchards prone to granulation (UC Pest Management Guidelines, www.ipm.ucdavis.edu/PMG/r107900311.html).

Only the cytokinin 6-benzyladenine (6-BA) (MAX-CEL®, Valent BioSciences) is registered for use on pistachio (*Pistacia vera* cv. Kerman). This is a result of technology developed to mitigate alternate bearing in pistachio (Lovatt and Ferguson, Calif. Pistachio Industry Annual Rep. Crop: 114-115, 2002). More than 30 years ago, the mechanism by which fruit number one year influences return bloom and yield the next year in pistachio was determined (Crane and Nelson, Hort Science, 6: 489-490, 1971). Alternate bearing results from excessive floral bud abscission in the on-crop year that begins with the initiation of embryo (nut) growth in June and intensifies during the period of rapid embryo growth in July, resulting in an off-bloom and off-crop the next year. This mechanism has been the focus of research into alternate bearing in pistachio ever since. Hormone concentrations within floral buds collected from on-crop trees (>70 fruit per cluster at the base of the shoot bearing the buds for next year's crop) were quantified. During the period of floral bud abscission, the ABA concentration of the buds increased while the cytokinin concentration decreased. The efficacy of foliar-applied 6-BA at 28 g/acre combined with low-biuret urea (46% N, 0.25% biuret) 2.8 kg N per acre per application was tested at the initiation of embryo growth (early June) and 30 days later (early July) to reduce floral bud abscission during the on-crop year to increase yield the following putative off-crop year. The 6-BA-urea strategy increased floral bud retention during several on-crop years 1.6- to 3.3-fold ($P \leq 0.05$), resulted in a 2.2-fold increase in yield of split nuts (dry weight) the following (off-crop) year (P=0.03), and increased 5-year cumulative yield of split nuts (dry weight) from 128.31 lbs (control) to 165.35 lbs per treated tree (P=0.02), for a 5-year cumulative net increase of 4,370 lbs split nuts (dry weight) per 118 trees per acre. This was a significant improvement, but it did not bring yield in the off-crop year close to the yield of an on-crop year.

There is only one PGR currently registered for use on avocado, naphthalene acetic acid (NAA) to inhibit shoot growth after pruning. Moreover, the continued registration of 2,4-D as a PGR is under review (Federal Register, Vol. 73, No. 248, 2008). If the registration of 2,4-D is cancelled, a new PGR to increase size of mandarin, mandarin hybrids, navel and Valencia orange fruit and to prevent pre-harvest fruit drop will be essential. The present disclosure meets the need in the art for compositions to mitigate alternate bearing in avocado, and meets the need in the art for alternatives to $GA_3$ and 2,4-D for use on mandarins. Furthermore, the present disclosure compliments technology for mitigating alternate bearing in pistachio.

After studying alternate bearing in citrus and avocado, research on alternate bearing in pistachio focused on the amount of summer vegetative shoot growth that follows the initial spring flush. For example, in pistachio, it is likely that the on-crop reduces the number and/or length of summer vegetative shoots that bear next year's floral buds, resulting in a reduced number of floral buds for next year's crop. As a result, despite the fact that the 6-BA-urea treatment can significantly increase floral bud retention, because fewer and shorter shoots are produced during the on-crop year, there are fewer buds that can be retained in response to the treatment and, thus, yield cannot be increased beyond this limiting factor and cannot reach the yield of on-crop trees. Preliminary hormone analyses revealed an increase in indole-3-acetic acid concentration and a reduction in zeatin riboside and isopentenyladenine concentration in pistachio buds during the period when pistachio fruit (developing embryo) exert their negative effect on return bloom. This result is consistent with inhibition of summer shoot growth in pistachio by correlative inhibition (high auxin concentration to low cytokinin concentration), and indicate that the compositions of the present disclosure would be suitable for mitigating alternate bearing in pistachio.

The present disclosure is compatible with the standard practices of the citrus, avocado and pistachio industries. Although PGRs, biostimulants, nutritional supplements and fertilizers are all subject to varying degrees of regulation by the Federal Environmental Protection Agency and state agencies, the compounds referred to in this disclosure are readily available. Since 6-BA has been previously exempted from the requirement of a residue tolerance for pistachio and apple, adenosine (adenine) is also likely to be exempted for these crops and others. Moreover, AMP, for which adenosine is a precursor, is categorized as a GRAS (Generally Recognized As Safe) compound.

The natural metabolite (adenosine and the like) of the present disclosure may be formulated with one or more of a pH stabilizer, an anti-oxidant, and an anti-microbial (or other compound for increasing shelf life). In addition, the natural metabolite can be formulated in a mixture with a carrier or, if necessary, other auxiliary agents to form any one of the standard types of preparations commonly used in agriculture, for example, a dry blend, granules, a wettable powder, an emulsion, an aqueous solution and the like.

Suitable solid carriers are clay, talc, kaolin, bentonite, terra abla, calcium carbonate, diatomaceous earth, silica, synthetic calcium silicate, kieselguhr, dolomite, powdered magnesia, Fuller's earth, gypsum and the like. Solid compositions can also be in the form of dispersible powders or grains, comprising, in addition to the natural metabolite, a surfactant to facilitate the dispersion of the powder or grains in liquid.

Liquid compositions include solutions, dispersions or emulsions containing the natural metabolite (adenosine and the like) together with one or more surface-active agents (surfactants) such as wetting agents, dispersing agents, emulsifying agents, or suspending agents. In those applications in which the compounds are applied as a foliar spray, surfactants are preferably used. Surfactants reduce the surface tension in the spray droplet to ensure that the material applied spreads out and covers the leaf surface rather than beading up. This facilitates absorption of the applied material into the plant. Surfactants can also affect the uptake of materials directly by changing the viscosity and crystalline structure of the waxes on the surface of the leaf or other tissues (Tue and Randall et al., Chapter 8-Adjuvants. In: Tu et al. [Eds.] Weed Control Methods Handbook: Tools and Techniques For Use In Natural Areas, The Nature Conservancy p. 219, 2001).

Generally, any number of surfactants may be used consistent with the purpose of this constituent. For example the surfactant can comprise a nonionic, anionic, cationic, or zwitterionic surfactant. The surfactant can be present in the composition of the disclosure as formulated or, alternatively, the surfactants can be introduced during administration to the plant. In such an instance, regardless of whether the administration is conducted via automated or manual means, the surfactant can be combined with the composition of the disclosure prior to, or co-dispensed separately. Cationic surfactants useful in compositions of the disclosure include but are not limited to amine ethoxylates, amine oxides, mono- and dialkylamines, imidazolinium derivatives, and alkylbenzyldimethylammonium halides. Nonionic surfactants useful in the context of this disclosure are generally polyether (also known as polyalkylene oxide, polyoxyalkylene or polyalkylene glycol) compounds. More particularly, the polyether compounds are generally polyoxypropylene or polyoxyethylene glycol compounds. Anionic surfactants useful with the disclosure comprise, for example, alkyl carboxylates, linear alkylbenzene sulfonates, paraffin sulfonates and secondary n-alkane sulfonates, sulfosuccinate esters and sulfated linear alcohols. Zwitterionic or ampho-teric surfactants useful with the disclosure include but are not limited to alpha-N-alkylaminopropionic acids, n-alkyl-alpha-iminodipropionic acids, imidazoline carboxylates, amine oxides, sulfobetaines and sultaines.

Although the surfactant can be present in the composition in any useful amount, in preferred embodiments, it is present in an amount from about 0.1% to about 25%, more preferably from about 0.1% to about 10% and more preferably still from about 0.5% to about 5%. A surfactant is present in the compositions of the disclosure in a useful amount when it facilitates the dissolution of the natural metabolite, enhances its uptake by the plant, and/or its effectiveness in inducing the desired response. In a preferred embodiment, the surfactant is a polysorbate, which is present in an amount from about 0.5% to about 5%. In a particularly preferred embodiment, the surfactant is polysorbate 20 (polyoxyethylene 20 sorbitan monolaurate), which is present in the composition in an amount from about 0.5% to about 5%.

The compositions of the disclosure can also contain suspending agents. Suitable suspending agents are, for example, hydrophilic colloids, for example polyvinylpyrrolidone and sodium carboxymethylcellulose, and the vegetable gums, for example, gum acacia and gum tragacanth.

Aqueous solutions, dispersions or emulsions may be prepared by dissolving the natural metabolite (adenosine or the like) in water or an organic solvent which can, if desired, contain one or more surface active, sticking, wetting, dispersing, or emulsifying agents. Suitable organic solvents are, for example, alcohols, hydrocarbons, oils and sulfoxides. In embodiments using alcohols, methanol, isopropyl alcohol, propylene glycol and diacetone alcohol are preferred. In embodiments using oils, petroleum oils are preferred. Of the sulfoxides, dimethylsulfoxide is preferred.

The compositions which are to be used in the form of aqueous solutions, dispersions or emulsions are generally supplied in the form of a concentrate containing a high proportion of the natural metabolite (adenosine or the like), and the concentrate is then diluted with water before use. These concentrates are usually required to withstand storage for prolonged periods and after such storage, to be capable of dilution with water in order to form aqueous preparations that remain homogeneous for a sufficient time to enable them to be applied by conventional spray equipment. In general, concentrates can conveniently contain from 10 to 60 percent by weight of the natural metabolite (adenosine or the like).

EXPERIMENTAL

The following examples are provided in order to demonstrate and further illustrate certain preferred embodiments and aspects of the present disclosure, and are not to be construed as limiting the scope thereof.

Abbreviations.

To ensure a complete understanding of this disclosure, the following abbreviations are provided: ABA (abscisic acid); Ado (adenosine); Ade (adenine); 6-BA (6-benzylaminopurine, 6-benzyladenine); 2,4-D (2,4-dichlorophenoxyacetic acid); 2,4,5-T (2,4,5-trichlorophenoxyacetic acid); GA (gibberellin); $GA_3$ (gibberrellic acid); IAA (indole-3-acetic acid); IBA (indole-3-butyric acid); IPA (isopentenyladenine); NAA (1-naphthaleneacetic acid); TIBA (2,3,5-triiodobenzoic acid); PGR (plant growth regulator); and Veg (vegetative).

Statistical Analysis.

All data were reported as mean number of shoots per 100 nodes unless stated otherwise. Analysis of variance was used to test for treatment effects on vegetative and floral shoot growth, floral intensity as the production of leafless and leafy floral shoots of mandarin and determinate and indeterminate floral shoots of avocado and vegetative shoots of both crop plants at bloom and yield of mandarin using the General Linear Models procedure of the SAS statistical program (SAS Inst. Inc., Cary, N.C.). Means were separated using Fisher's protected LSD or Dunnett's two-tailed T-test at P=0.05.

Example 1

Administration of Adenosine by Trunk Injection to Mitigate Alternate Bearing in Mandarin Trees This example describes the mitigation of alternate bearing in 'Nules' Clementine mandarin trees achieved via trunk injection of adenosine in a composition containing the auxin transport inhibitor TIBA. On-crop 'Nules' Clementine mandarin trees received trunk injections of the following compounds listed in Table 1-1: TIBA (2,3,5-triiodobenzoic acid) (Sigma Chemical); 6-BA (6-benzyladenine) (Sigma Chemical); $GA_3$ (PROGIBB® 40%, Valent BioSciences Corp.); and Ado (9-beta-D-adenosine) (Sigma Chemical, Catalog No. A9251) alone or in combination with TIBA. Each material was supplied at the rate of 1 g per tree dissolved in 50-60 ml distilled water using two plastic syringes per tree at each application time. Application times were timed (1) to stimulate summer shoot growth by overcoming correlative inhibition (July) and (2) to overcome inhibition of spring bud break (January). Thus, trees were treated in July alone or in July and January. There was also a treatment in which the apical three nodes of each shoot were removed to release the lateral buds from the dominance of the apical bud to promote summer vegetative shoot growth. The treatments included untreated on-crop control trees and untreated off-crop control trees. The experimental design was a randomized complete block with 5 individual tree replications per treatment with 13 treatments. For each tree, branches (12 inches long), 3 with fruit and 1 branch without fruit in each of the four tree quadrants, were tagged (off-crop control trees were tagged 3 without fruit and 1 with fruit). At the end of September and December, the number and length of new vegetative shoots were quantified to determine the capacity of treatments to overcome inhibition of buds that produce the summer and fall flush shoots, respectively. During spring bloom, the number of floral shoots (leafy and leafless), vegetative shoots and inactive buds on each tagged branch were counted on the summer/fall flush and the previous year's spring flush.

TABLE 1-1

Effect of trunk injections on spring bloom of on-crop Mandarin trees.

| Treatment | Time | Floral | Leafy Floral | Leafless Floral | Floral on Summer-Fall | Floral on Spring |
|---|---|---|---|---|---|---|
| | | | No. of shoots per 100 nodes | | | |
| Off-crop control | | 23 ab[z] | 21 ab | 3 | 28 ab | 14 b |
| On-crop control | | 7 cde | 3 cd | 4 | 10 cd | 3 bc |
| TIBA | July | 19 bc | 13 bcd | 5 | 27 ab | 3 bc |
| 6-BA | July | 12 bcde | 9 bcd | 2 | 17 abcd | 3 bc |
| $GA_3$ | July | 3 de | 3 cd | 0 | 4 d | 0 c |
| Ado | July | 10 cde | 8 cd | 2 | 14 bcd | 2 bc |
| Ado + TIBA | July | 15 bcd | 11 bcd | 4 | 22 abc | 4 bc |
| A3- | July | 5 de | 3 cd | 2 | 5 d | 3 bc |
| TIBA | Jul + Jan | 18 bc | 15 bc | 3 | 26 abc | 5 bc |
| 6-BA | Jul + Jan | 7 cde | 6 cd | 1 | 9 cd | 2 bc |
| $GA_3$ | Jul + Jan | 1 e | 1 d | 0 | 2 d | 0 c |
| Ado | Jul + Jan | 12 bcde | 12 bcd | 0 | 16 bcd | 5 bc |
| Ado + TIBA | Jul + Jan | 32 a | 31 a | 1 | 33 a | 33 a |
| P-value | | 0.0005 | 0.0006 | 0.3227 | 0.0033 | 0.0006 |

[z]Means within a column followed by a different letter are significantly different at specified P-value by Fisher's Protected LSD. Values followed by different letters are significantly different from each other, whereas those having a letter in common are not.
A3- = apical 3 nodes removed.

Table 1-1 summarizes the effect of July and July plus January adenosine and PGR trunk injections and removal of the apical three nodes on spring bloom of on-crop 'Nules' Clementine mandarin. These data indicate that when adenosine and TIBA were applied twice (first in July and a second time in January), alternate bearing was mitigated, wherein the number of floral shoots borne on summer/fall shoots was significantly increased over that of the on-crop trees and now equal to the number floral shoots on the summer/fall shoots of off-crop trees. Moreover, the significant increase in floral shoots was of the type known as "leafy" floral shoots, which have a higher potential to set fruit that persist to harvest than "leafless" floral shoots.

Additionally, the treatment increased the number of floral shoots produced on the previous year's spring flush shoots to a greater number than all other treatments even exceeding the number of the off-crop control trees.

Example 2

Administration of Adenosine by Trunk Injection to Mitigate Alternate Bearing in Avocado Trees This example describes the mitigation of alternate bearing in 'Hass' avocado trees achieved via trunk injection of adenosine and plant growth regulators. The following treatments were injected (1 g/tree) in mid-January into the trunk of on-crop 'Hass' avocado trees in a commercial orchard in Irvine, Calif.: (1) 9-beta-D-adenosine (Sigma Chemical, Catalog No. A9251); (2) 6-BA (Sigma Chemical); (3) $GA_3$ (PROGIBB® 40%, Valent BioSciences Corp.); (4) TIBA (Sigma Chemical); and (5) TIBA plus adenosine. Each material was supplied at the rate of 1 g per tree dissolved in 50-60 ml distilled water using two plastic syringes per tree. There were five individual tree replicates per treatment, including (6) untreated on-crop control trees. For each tree, branches (12 inches long), 1 with fruit and 1 branch without fruit in each of the four tree quadrants, were tagged. During spring bloom, the number of floral shoots (indeterminate and determinate), vegetative shoots and inactive buds on each tagged branch were counted.

which remained on the tree through the standard time of harvest, is given in the last column of Table 2-1. Since there were only five individual tree replications for each treatment, yield results are not statistically significant at the 5% level, but the results indicate a positive effect (a minimum of 20 individual tree replications is required to demonstrate that a treatment has a statistically significant effect on yield for the 'Hass' avocado due to a high degree of variability in yield per tree).

Example 3

Administration of Adenosine by Foliar Spray to Increase Yield of Commercially Valuable Large Size Fruit in Alternate Bearing Mandarin Trees This example describes the increase in yield of commercially valuable large size fruit of alternate bearing Clementine mandarin trees achieved by canopy application of adenosine. In this example evidence is provided that adenosine applied as a canopy spray to stimulate summer vegetative shoot growth during the mitigation of alternate bearing also results in an increase in fruit size and yield of commercially valuable fruit to mitigate the problem of small fruit size frequently associated with on-crop fruit. Adenosine (9-beta-D-adenosine) obtained from Sigma Chemical Co. (Catalog No. A9251) (25 mg/L in 250 gallons of water per acre) was applied one time at maximum peel thickness,

TABLE 2-1

Effect of trunk injections on spring bloom of 'Hass' avocado trees bearing an on-crop and yield of the putative off-crop following the on-crop.

| Treatment | Time | Floral | Determinate floral | Indeterminate floral | Floral (with fruit) | Floral (w/o fruit) | Fruit yield No. per tree |
|---|---|---|---|---|---|---|---|
|  |  | No. of shoots per 100 nodes |  |  |  |  |  |
| On-crop control | Jan | 6 b$^z$ | 1 b | 5 | 5 c | 7 | 172 |
| Ado | Jan | 10 ab | 3 ab | 7 | 8 abc | 10 | 220 |
| 6-BA | Jan | 9 b | 1 b | 8 | 9 abc | 9 | 169 |
| $GA_3$ | Jan | 7 b | 2 b | 6 | 6 bc | 8 | 194 |
| TIBA | Jan | 9 b | 1 b | 8 | 11 ab | 8 | 478 |
| Ado + TIBA | Jan | 15 a | 8 a | 7 | 12 a | 16 | 262 |
| P-value |  | 0.0693 | 0.0789 | 0.2906 | 0.0793 | 0.1618 | 0.1404 |

$^z$Means within a column followed by a different letter are significantly different at specified P-value by LSD Test.

Table 2-1 summarizes the effect of January adenosine and plant growth regulator (PGR) trunk injections on spring bloom of on-crop 'Hass' avocado trees. These indicate adenosine combined with TIBA as a single trunk injection to on-crop trees in January overcame the inhibitory effect of the fruit on bud break in spring and significantly increased the number of floral shoots compared to the untreated on-crop control trees. The treatment significantly increased the number of determinate floral shoots (inflorescences), which are typically in low number or absent in the off-crop year bloom. Moreover, the treatment significantly increased floral shoot number on the branches bearing fruit, bringing the number of floral shoots on branches with fruit, where the fruit have a direct inhibitory effect on buds, to that of branches without fruit, where inhibition of bud break would be expected to be less. Note that the efficacy of adenosine alone was equal to that of adenosine plus TIBA in increasing the total number of floral shoots per 100 nodes, but not significantly different from the untreated on-crop control. Adenosine administered in July and again in January is contemplated to increase total floral shoot number to a value significantly greater than the untreated on-crop control trees. The number of fruit set, which marks the end of the cell division stage of citrus fruit development, to 'Fina Sodea' Clementine mandarin trees. As shown in Table 3-1 below, application of adenosine significantly increased the 3-year cumulative yield of fruit 57.16 to 69.85 mm in diameter (packing carton sizes large and jumbo) and increased the 3-year cumulative yield of commercially valuable mandarin fruit in the combined pool for fruit of packing carton sizes large, jumbo and mammoth, without reducing total yield (average kilograms [quantity× size] per tree) (P≤0.05). As shown in Table 3-2 below, application of adenosine significantly increased the quantity of large size fruit per tree as the 3-year cumulative number of fruit 57.16 to 69.85 mm in diameter (packing carton sizes large and jumbo) and the 3-year cumulative number of commercially valuable mandarin fruit in the combined pool for fruit of packing carton sizes large, jumbo and mammoth) without reducing total yield (average number of fruit per tree) (P≤0.05).

TABLE 3-1

Effect of adenosine applied to the canopy of mandarin trees on yield of fruit in different size classes in kilograms per tree.

| Treatment | Total | Colossal | Mammoth | Jumbo | Large | Medium | Small | Ma + J + L |
|---|---|---|---|---|---|---|---|---|
| | | | | Total kg/tree | | | | |
| Adenosine | 126.30[y] | 1.04 | 3.52 | 15.42 a | 34.67 a | 37.00 | 23.58 | 53.60 |
| Control | 110.88 | 1.28 | 4.15 | 10.47 b | 28.24 b | 36.94 | 24.37 | 42.86 |
| T-test | NS | NS | NS | * | * | NS | NS | * |

[z] Fruit size categories based on fruit transverse diameters (mm): small (44.45-50.80), medium (50.81-57.15), large (57.16-63.50), jumbo (63.51-69.85), mammoth (69.86-76.20), colossal (76.21-82.55), and large + jumbo + mammoth (57.16-76.20). Ma + J + L is the sum of mammoth, jumbo and large fruit.
[y] Average weights followed by different letters are significantly different at P = 0.05 based on Dunnett's two-tailed T-test as indicated with an asterisk; means that are not significantly different are indicated by NS.

TABLE 3-2

Effect of adenosine applied to the canopy of mandarin trees on quantity of fruit in different fruit size classes.

| Treatment | Total | Colossal | Mammoth | Jumbo | Large | Medium | Small | Ma + J + L |
|---|---|---|---|---|---|---|---|---|
| | | | | Total fruit no./tree | | | | |
| Adenosine | 1529.3[y] | 5.64 | 22.89 | 128.25 a | 360.93 a | 497.05 | 417.12 | 512.07 a |
| Control | 1467.0 | 6.78 | 26.94 | 86.53 b | 292.66 b | 493.79 | 431.69 | 406.14 b |
| T-test | NS | NS | NS | * | * | NS | NS | * |

[z] Fruit size categories based on fruit transverse diameters (mm): small (44.45-50.80), medium (50.81-57.15), large (57.16-63.50), jumbo (63.51-69.85), mammoth (69.86-76.20), colossal (76.21-82.55), and large + jumbo + mammoth (57.16-76.20). Ma + J + L is the sum of mammoth, jumbo and large fruit.
[y] Average fruit numbers followed by different letters are significantly different at P = 0.05 based on Dunnett's two-tailed T-test.

TABLE 3-3

Effect of adenosine applied to the canopy of 'mandarin trees on fruit value (cumulative income in U.S. dollars).

| Treatment | Totally | Small | Medium | Large | Jumbo | Mammoth | L + J + Ma |
|---|---|---|---|---|---|---|---|
| | | | | US$/acre | | | |
| Adenosine | 8015.80 | 1497.80 | 2522.40 | 2584.10 a | 1149.50 a | 262.10 | 3995.60 a |
| Control | 7264.50 | 1550.90 | 2518.60 | 2105.20 b | 780.70 b | 309.10 | 3195.00 b |
| P-value | 0.1179 | 0.8130 | 0.9088 | 0.0723 | 0.0737 | 0.6982 | 0.0645 |
| Dunnett | NS | NS | NS | * | * | NS | * |

[z] Fruit size categories based on fruit transverse diameters (mm): small (44.45-50.80), medium (50.81-57.15), large (57.16-63.50), jumbo (63.51-69.85), mammoth (69.86-76.20), and large + jumbo + mammoth (57.16-76.20). Fruit were packed by number (based on size) per 11 kg box. Fruit count per box was: small, 40; medium; 34, large, 26; jumbo, 19.5; and mammoth 15. Average US dollars per box (retail) of fruit of each size category was: tiny, $0; small, $3.50; medium, 3.75; large, $4.10; jumbo, $4.10; mammoth, $4.10; colossal, $0; and super colossal, $0. Dollar values are based on the 3-year average FOB prices supplied by large grower, packer shipper of mandarins in the Central San Joaquin Valley, Calif. Values are based on 200 trees per acre.
[y] Total is the sum of small, medium, large, jumbo, and mammoth values.
* Values differ significantly from that of the control at P = 0.05 based on Dunnett's two-tailed T-test.

These data highlight the production benefits of adenosine applied to stimulate summer shoot growth (maximum peel thickness). There was a statistically significant net increase in 3-year cumulative yield of commercially valuable large fruit (57.16-76.20 mm in diameter) of 4,735 lbs/200 trees/acre. There was no reduction in total yield; the adenosine-treated trees had a numerical (non-significant) net increase of 6,799 lbs fruit/200 trees/acre. These data were also significant when averaged across the three years of the experiment using repeated measures analysis, establishing that adenosine had a positive effect each year. This type of analysis is used to demonstrate average effects across years in a single orchard. Use of foliar-applied adenosine to increase fruit size and to increase the yield of commercially valuable fruit is expected to compare favorably to untreated controls, as well as standard available practices: (1) $GA_3$ (PROGIBB 4%, Valent BioSciences Corp.) at 1-8 fluid oz per 100 gallons of water, using a sufficient number of gallons for good coverage; 1-2 applications from 50% petal fall to 3 weeks after petal fall of mandarins and mandarin hybrids; (2) 2,4-D (CITRUSFIX® AmVac Corp.) 0.67 oz (3.34 lbs 2,4-D isopropylester/gallon) per 100 gallons of water at 500 gallons per acre 21 to 35 days after 75% petal fall of mandarins and mandarin hybrids; and (3) 1% low-biuret urea applied at maximum peel thickness. PROGIBB® must be used with caution as it may result in more fruit set than is desirable resulting in a reduction in final fruit size. In addition it may result in leaf drop in trees under stress. Adenosine in a does not require this caution and its efficacy in increasing yield of commercially valuable fruit is not as sensitive to crop load (alternate bearing) as that of $GA_3$. Likewise, CITRUSFIX® must be used with caution as it may cause fruit dryness, especially in 'Nules' and other cultivars that tend to be dry or granulated. In addition, CITRUSFIX® cannot be used on trees less than 6 years old and cannot be used during a flush of leaf growth. Adenosine does not require these cautions. Adenosine did not have negative effects on mandarin fruit quality and in one of the three years of the research had the desirable effects of reducing acidity and increasing the ratio of total soluble solids (sugars) to acid.

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are understood by those skilled in the art are intended to be within the scope of the claims.

We claim:

1. A composition effective in mitigating alternate bearing in a perennial crop plant, comprising: (i) a purified adenosine comprising 9-beta-D-adenosine, (ii) and an auxin transport inhibitor, wherein the auxin transport inhibitor is 2,3,5-triiodobenzoic acid; or
   a flavonoid or isoflavanoid selected from the group consisting of naringenin, quercetin, formononetin, and genistein; and,
   wherein, the 9-beta-D-adenosine and the auxin transport inhibitor are more effective in mitigating alternate bearing when applied to the perennial crop plant in combination than 9-beta-D-adenosine alone.

2. The composition of claim 1, further comprising a fertilizer.

3. The composition of claim 1, wherein the plant growth regulator is 2,3,5-triiodobenzoic acid.

4. The composition of claim 1, wherein the auxin transport inhibitor is naringenin.

5. The composition of claim 2, wherein the fertilizer is selected from the group consisting of nitrogen, potassium, magnesium, phosphorus, calcium, sulfur, iron, boron, chlorine, manganese, zinc, copper, molybdenum, nickel, selenium, silicon, cobalt, and combinations thereof.

6. The composition of claim 2, wherein the fertilizer is low-biuret urea.

7. The composition of claim 2, wherein the fertilizer is disodium octaborate tetrahydrate.

8. The composition of claim 1, wherein the composition is an aqueous solution comprising water.

9. The composition of claim 1, wherein the composition further comprises an amino acid.

10. The composition of claim 1, wherein the composition further comprises a surfactant.

11. The composition of claim 1, wherein the composition further comprises a pH stabilizer.

12. The composition of claim 1, wherein the composition further comprises an anti-oxidant.

* * * * *